United States Patent [19]

Takahashi et al.

[11] Patent Number: 4,518,464
[45] Date of Patent: May 21, 1985

[54] METHOD OF DETECTING EMBRITTLEMENT OF HEAT-RESISTING STEEL

[75] Inventors: Hideaki Takahashi; Tetsuo Shoji, both of Sendai; Kiyoshi Saitoh, Yokohama; Masamitsu Muramatsu, Sagamihara; Kazushige Kimura, Chigasaki, all of Japan

[73] Assignees: Kabushiki Kaisha Toshiba, Kawasaki; Hideaki Takahashi; Tetsuo Shoji, both of Sendai, all of Japan

[21] Appl. No.: 627,832

[22] Filed: Jul. 5, 1984

[30] Foreign Application Priority Data

Jul. 6, 1983 [JP] Japan ................. 58/122566

[51] Int. Cl.³ ............................................. G01N 27/46
[52] U.S. Cl. ..................................... 204/1 T; 204/400; 204/404
[58] Field of Search ................ 204/1 T, 1 C, 400, 404

[56] References Cited

U.S. PATENT DOCUMENTS

| | | | |
|---|---|---|---|
| 2,886,497 | 5/1959 | Butler | 204/1 T |
| 3,375,183 | 3/1968 | Banks et al. | 204/196 |
| 3,428,532 | 2/1969 | Banks | 204/1 T |
| 4,019,129 | 4/1977 | Grau | 204/1 T |
| 4,063,644 | 12/1977 | Hoffman et al. | 204/1 T |
| 4,132,605 | 1/1979 | Tench et al. | 204/1 T |
| 4,160,702 | 7/1979 | Baxter | 204/1 T |
| 4,179,349 | 12/1979 | Park | 204/404 |
| 4,221,651 | 9/1980 | Mansfeld et al. | 204/404 |
| 4,445,988 | 5/1984 | Steeves | 204/1 T |
| 4,455,212 | 6/1984 | Baxter | 204/1 T |

*Primary Examiner*—T. Tung
*Attorney, Agent, or Firm*—Schwartz, Jeffery, Schwaab, Mack, Blumenthal & Koch

[57] ABSTRACT

A method of detecting embrittlement of a heat-resisting steel comprises evaluating the brittleness of the heat-resisting steel on the basis of the repassivation current value obtained by (a) connecting the steel as the anode of an anode polarization curve measuring apparatus wherein an aqueous solution containing an organic acid and an alkylbenzene sulfonic acid or its salt is used as an electrolytic solution; and (b) raising the anode potential from an active region to a passive region and thereafter lowering the anode potential to measure the repassivation current value.

4 Claims, 9 Drawing Figures

METHOD OF DETECTING EMBRITTLEMENT OF HEAT-RESISTING STEEL

BACKGROUND OF THE INVENTION

The present invention relates to a method of detecting embrittlement, such as embrittlement due to passage of time, of heat-resisting steels, and more particularly to a method wherein an anode polarization curve for heat-resisting steel products is prepared to determine repassivation current values, and embrittlement of the heat-resisting steel products is detected on the basis of these repassivation current values.

Heat-resisting steels must be chemically stable at high temperatures, have good mechanical properties, and have structures which are stable at high temperatures. However, in the case of steam turbines and the like used over a long period of time, structural changes occur in the heat-resisting steel, and deterioration with time of the material is liable to become marked. Of the items of such deterioration of the material, a particularly problematic item is the so-called temper brittleness with age.

It is believed that this temper brittleness with passage of time occurs as a result of the same causes as those of temper brittleness arising in the tempering step of heat treatment by the repetition for a long period of time of heating at high temperatures during operation and cooling during suspension of operation. That is, it is believed that the temper brittleness with passage of time occurs because the impurity elements such as Sb, As, P and Sn present in steel, particularly P, segregate in the grain boundary to reduce the strength of the grain boundary. This is apparent from the fact that an electron microscope shows that the impact fractured surface of the embrittled materials is the fractured surface of the grain boundary, and from the fact that the elemental spectra of the fractured surface of the grain boundary by means of an Auger electron spectral analysis show that the impurity elements such as P segregate in the grain boundary.

When the secular temper brittleness of the heat-resisting steel products occurs, there is the possibility that it will lead to deficiencies, e.g., breakage of these steel products. Particularly, in the case of turbine rotors and the like, which must be rotated at a high velocities and withstand large centrifugal forces, a serious trouble can occur in the steam turbine. Accordingly, for quality evaluation of heat-resisting steels and trouble prevention, a variety of methods of detecting temper brittleness with age have been proposed.

Hitherto, the following methods of detecting the degree of temper brittleness of steels have been proposed. It is possible to detect temper brittleness in a steel by subjecting a sample of the steel to an impact test to determine the degree of reduction of impact value (the reduction of the value of energy absorbed). It is also possible to detect temper brittleness in terms of the shifting of a test temperature-impact value curve toward the higher temperature slide, i.e., the shifting of the transition temperature of an impact value. Further, it is possible to detect the temper brittleness by the rise in the fracture transition temperature which is defined as the temperature obtained by measuring the ratio of the ductile fracture area to the total fracture area of the fractured surface of a test piece which has been impact fractured to determine the ductile fracture percentage and taking the temperature corresponding to a ductile fracture percentage of 50% from the temperature dependency.

However, all of these prior methods of detecting temper brittleness are destructive tests wherein it is impossible to carry out such tests unless a test piece is cut off from a heat-resisting steel product which is the subject to be inspected. Therefore, it is impossible to use the steel product again after inspection, and thus it is practically impossible to detect temper brittleness during periodical inspection for the purpose of the maintenance of heat-resisting steel products.

SUMMARY OF THE INVENTION

In view of the difficulties described above, we have carried out studies directed toward overcoming them. An object of the present invention is to provide a nondestructive method of detecting the temper brittleness of a heat-resisting steel product.

According to the results of our studies, it has been found that an electrochemical method, which comprises preparing an anode polarization curve for a heat-resisting steel and detectng the temper brittleness of the heat-resisting steel on the basis of information obtained from this anode polarization curve, is effective for achieving the above stated object.

More particularly, an anode polarization curve for a heat-resisting steel is obtained by: using the heat-resisting steel which is in contact with an electrolytic solution as an anode and an electrode of platinum and the like as a counter electrode; applying the potential difference across the two electrodes from an external power source; and plotting the potential imparted to the anode which is the heat-resisting steel and the current flowing between the two electrodes.

In the preparation of an anode polarization curve, when the anode potential is present in the range of from natural potential to an active region, the anode metal is dissolved in the electrolytic solution with increase in the anode potential, and thus the current value becomes large. However, when the anode potential is increased up to a passive region, the current rapidly decreases to exhibit a passivation current. This is because a passive film is formed on the anode surface. Accordingly, a change of the texture of the metal surface which is an anode affects the formation of the passive film to vary the passivation current value. Therefore, it is possible to determine the change of the anode metal texture and the texture change due to temper brittleness by examining this passivation current value.

We have carried out extensive studies on the basis of this discovery. As a result, we have found that the magnitude of the repassivation current value appearing when an anode potential is once increased up to a passive region and thereafter is again lowered is intimately related to the presence or absence of temper brittleness. Further, it has been found that it is preferable to use an aqueous solution containing an organic acid and an alkylbenzene sulfonic acid or its salt as an electrolytic solution.

The present invention relates to a method of detecting embrittlement of a heat-resisting steel which comprises evaluating the temper brittleness of the heat-resisting steel on the basis of a repassivation current value obtained by the steps of:

(a) connecting the heat-resisting steel as an anode of an anode polarization curve-measuring apparatus wherein an aqueous solution containing an organic acid and an alkylbenzene sulfonic acid or its salt is used an electrolytic solution; and (b) raising the anode potential from an active region to a passive region and thereafter lowering this potential to detect the repassivation current value.

DETAILED DESCRIPTION OF THE INVENTION

A subject to be inspected according to the detection method of the present invention is a heat-resisting steel. A heat-resisting steel subject to the possibility of acquiring secular temper brittleness in the composition thereof when it is used at a temperature of from about 300° to about 600° C., is a subject of the present invention. Heat-resisting steels which are subjects of the present invention are, for example, low-alloy heat-resisting steels such as C-Mo, Si-Cr, Si-Cr-Mo, Cr-Mo, Cr-Mo-V, Ni-Mo-Cr-V and Mo-V steels, medium Cr heat-resisting steels such as 10–13% heat-resisting steel and high Cr heat-resisting steels according to the chemical component classification, and martensite, ferritic, and austenite heat-resisting steels according to the textural classification.

An electrolytic solution of the present invention is an aqueous solution containing an organic acid and an alkylbenzene sulfonic acid or salt thereof. The blend ratio of the organic acid and the alkylbenzene sulfonic acid or salt thereof and the concentrations of these compounds can vary depending upon the type of the steels which are the subject to be inspected, the pH of an electrolytic solution, and methods of preparing the polarization curve. Thus it is possible to select the blend ratio and concentration which are optimum depending upon these factors.

Picric acid, benzoic acid, phthalic acid, isophthalic acid, terephthalic acid, oxalic acid, malonic acid, succinic acid, glutaric acid, acetic acid, propionic acid, butyric acid and the like can be used as the organic acid. Of these compounds, picric acid is particularly preferred.

Alkylbenzene sulfonic acids such as trimethylbenzene sulfonic acid, triethylbenzene sulfonic acid and dodecylbenzene sulfonic acid and their sodium salts, potassium salts and the like can be used as the alkylbenzene sulfonic acid or salt thereof. Of these compounds, sodium trimethylbenzene sulfonate is preferred.

Further, it is desirable that the organic acid and the alkylbenzene sulfonic acid or its salt be used in such quantities that the alkylbenzene sulfonic acid or its salt is present in an amount of from 0.01 to 10 moles, preferably from 0.5 to 5 moles, and more preferably from 0.7 to 1.5 moles, per mole of the organic acid.

Furthermore, in order to promote the reaction or to adjust the pH of the electrolytic solution, acids, bases and salts as well as other additives can be optionally added to the electrolytic solution of the present invention in addition to the solute described above. While in the case of sodium trimethylbenzene sulfonates there are five isomers, any of these isomers may be used in the electrolytic solution of the present invention.

Figure 1:
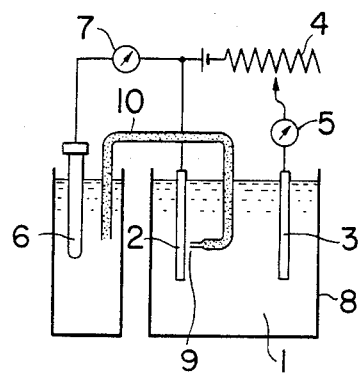
FIG. 1 is a schematic elevation illustrating an apparatus circuit for the measurement of polarization curves.

An apparatus for measuring current-potential which operates on the same principle as that of a measurement circuit used for the preparation of a polarization curve as shown in FIG. 1 is used for measuring polarization curves in the present invention. More specifically, a piece of a heat-resisting steel which is a sample to be tested is positioned as an anode 2 to confront a counter electrode 3 in an electrolytic solution 1. The two electrodes are connected to an external power source 4 to provide a potential. The current flowing through a circuit is directly measured by means of an ammeter 5, and the potential of the sample is measured by means of a potentiometer 7 on the basis of a reference electrode 6. In the apparatus shown in FIG. 1, in order to minimize disorder of the electric field generated by inserting the reference electrode into an electrolytic bath 8, a Luggin capillary tube 9 is brought near the face of the electrode 2, and this capillary tube and the reference electrode 6 outside of the electrolytic bath 8 are connected via a salt bridge 10.

The apparatus for the measurement of polarization curves according to the present invention is not limited to the apparatus shown in FIG. 1, and modified apparatuses may be used. When the subject to be inspected is a large-size heat-resisting steel article which cannot be easily moved, a portable measurement apparatus is desirable.

A method which includes the detection of "a repassivation current" defined hereinafter, in other words, a method of preparing a polarization curve according to the present invention will be described.

Dust and the like deposited on the surface of an inspection portion of the heat-resisting steel which is a subject to be inspected are removed, and the heat-resisting steel is connected as an anode to an apparatus for the measurement of anode polarization curves to cause the electrolytic solution to contact the surface of the inspection portion. The potential difference is produced between the anode and the counter electrode (cathode) by an external direct-current power source to cause a current to flow between the anode and the counter electrode. In this case, the anode potential and current (or current density) are measured by a potentiometer and an ammeter, respectively.

Figure 2:
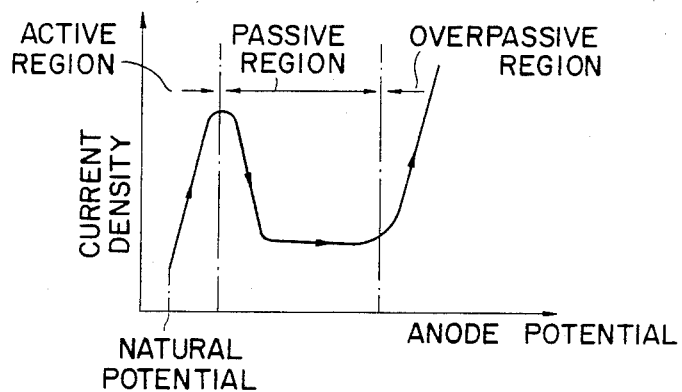
FIG. 2 is a graph of an anode polarization curve indicating variation of current density with potential.

Further, the anode potential is gradually raised and the accompanying variation in the current (current density) is measured. This is repeated to obtain a current-potential curve (anode polarization curve). FIG. 2 is a general graph showing an anode polarization curve for iron. As shown in FIG. 2, when the anode potential is raised from the natural potential, the anode metal is dissolved into the electrolytic solution in the active region to increase the current (current density) with increase of the potential. However, when the anode potential is further raised, the anode potential reaches a passive region in which the anode surface is covered with a passive film, and therefore the current rapidly decreases.

When the anode potential is further raised, it reaches an overpassive region to generate oxygen, and therefore the current increases again. By the terms "active region" and "passive region" as used herein are meant the regions described above.

Methods of preparing a polarization curve include, generally, a steady method and a non-steady method. In the steady method, a constant potential ordinarily is created at the anode by using a potentiostat, and it is confirmed that the current value does not vary during a specific time period, the measured value being regarded as a current which corresponds to the anode potential. In the non-steady method (potential scanning method), the anode potential is varied with time at a constant potential scanning velocity (mV/minute), and currents corresponding to respective potentials are measured.

In general, while the current values measured by the non-steady method are higher than those measured by the steady method, the potential values in the active region, the passive region and the overpassive region are substantially identical in the steady method and the non-steady method, and the shapes of the polarization curves are similar. Accordingly, either of the steady method and the non-steady method may be used in the present invention. However, the non-steady method which is capable of carrying out the inspection rapidly is preferable to the steady method which requires some time to reach a steady state.

In the method of the present invention, the anode potential is raised from an active region to a passive region, and then this electrode potential is lowered to carry out a potential-current measurement. Accordingly, while it is unnecessary to raise the anode potential to the overpassive region, the anode potential must be lowered after it has reached the passive region.

By the term "repassivation current" as used herein is meant the minimum value of the current appearing when the anode potential is again lowered after it has been raised from the active region to the passive region. It is believed that the reason why the current decreases further to assume the minimum value when the anode potential is lowered is that the passive film formed when the anode potential is raised to the passive region is converted into a stronger passive film by the lowering of the anode potential.

Figure 3:
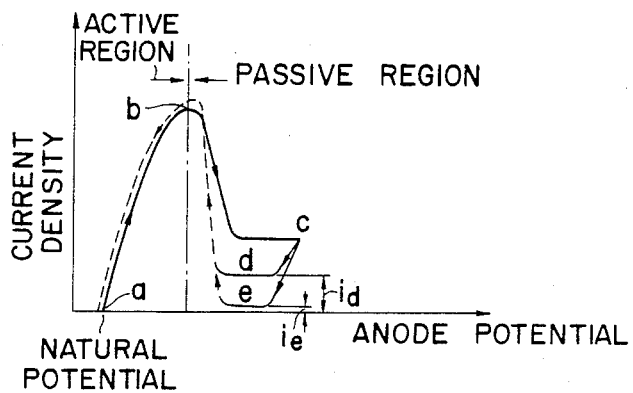
FIG. 3 is a graph similar to FIG. 2 indicating an example of a polarization curve according to the present invention.

FIG. 3 is a view illustrating a polarization curve prepared according to the method of the present invention. In FIG. 3, as described in conjunction with FIG. 2, when the anode potential is gradually raised from the portion in the vicinity of the natural potential "a", the current increases in the active region and reaches a maximum active current point "b". Thereafter, when the anode potential is further raised, it reaches the passive region, and the current decreases rapidly. When the anode potential is raised to a point "c" and then decreased, the current decreases to reach a minimum portion.

When temper brittleness does not occur in a heat-resisting steel which is the subject to be inspected, the repassivation current $i_e$ shown at the minimum portion "e" is zero or a value near zero. On the contrary, when temper brittleness occurs in the heat-resisting steel, the repassivation current $i_d$ shown at the minimum portion "d" is of a higher value. Thus the variation of the repassivation current depending on the presence or absence of temper brittleness may be attributed to the following reason. Phosphorous segregates in the grain boundary present in the texture of a temper embrittled material, whereby no passive film is formed on the surface of the grain boundary portion, which is activated, whereas in the case of absence of temper brittleness, the passive film is formed on the entire surface.

Accordingly, it is also possible to evaluate qualitatively whether or not the embrittlement in question occurs by detecting the magnitude of the repassivation current. The quantitative evaluation of the embrittlement can also be carried out in the following manner, for example. With respect to a standard material of which the degree of tempering with age is known, the repassivation current is measured beforehand. The level of the repassivation current of the subject of which the degree of a temper brittleness is not known is measured, and then both repassivation current values are compared to evaluate the degree of embrittlement.

While the present invention will now be described in detail by way of the following Examples, it is to be understood that the present invention is not intended to be limited in scope by these Examples.

EXAMPLE 1

With respect to test pieces collected from an intermediate pressure stage portion of a CrMoV steel steam turbine rotor which had been used for 20 years, an anode polarization curve was prepared by the potential scanning process according to the present invention. The intermediate pressure stage had been used at a temperature of 538° C. and exhibited temper brittleness. The test piece had the composition shown in Table 1 with respect to the main chemical components.

| Chemical Components (% by weight) | | | | | | |
|---|---|---|---|---|---|---|
| C | Mn | P | Ni | Cr | Mo | V |
| 0.31 | 0.80 | 0.028 | 0.45 | 1.01 | 1.25 | 0.23 |

An aqueous solution containing $2 \times 10^{-2}$ moles/liter of picric acid and $1 \times 10^{-2}$ moles/liter of sodium trimethylbenzene sulfonate was used for the electrolytic solution.

Figure 4:
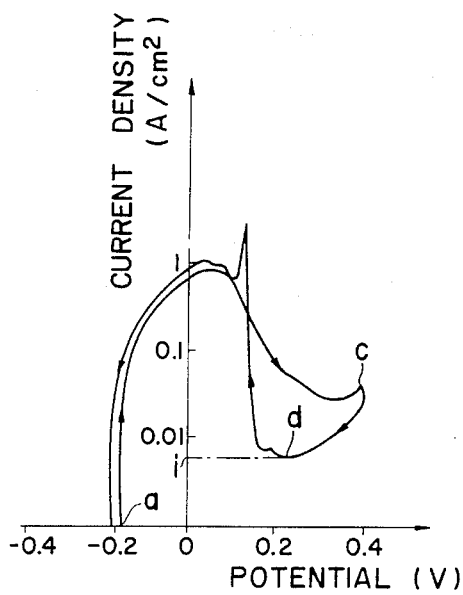
FIG. 4 is a similar graph of a polarization curve obtained in Example 1 set forth hereinafter.

After the measurement apparatus was assembled, the potential of the anode (test piece) was swept from a natural potential "a" to a potential of 0.4 V in the passive region at a scanning velocity of 1 mV/minute and retained for 2 minutes at a sweep inversional point "c" (potential of 0.4 V). Then the potential of the anode was conversely swept to the portion near the natural potential "a" at a scanning velocity of 1 mV/minute. An anode polarization curve was prepared from the current-potential values (abscissa: voltage in V; ordinate: current density in mA/cm²). The results are shown in FIG. 4.

EXAMPLE 2

An anode polarization curve was prepared as in Example 1 except that the test piece was collected from a coupling portion which was a portion of the same steam turbine rotor as that of Example 1, and the temperature used was about room temperature.

Figure 5:
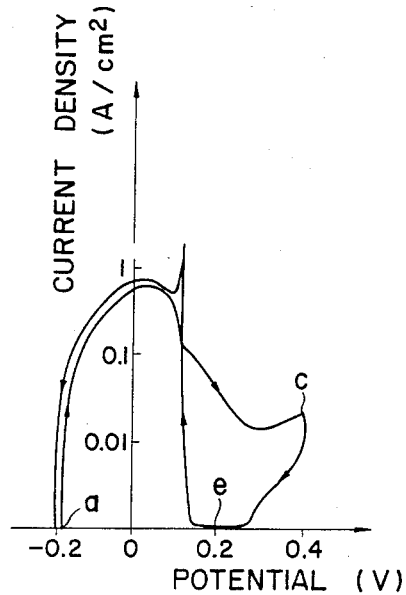
FIG. 5 is a similar graph of a polarization curve obtained in Example 2.

The anode polarization curve obtained is shown in FIG. 5.

EXAMPLE 3

An anode polarization curve was prepared as in Example 1 except that, while the test piece was collected from the same intermediate pressure stage portion as that of Example 1, it was subjected to a de-embrittling treatment wherein the test piece was retained for 2 hours at a temperature of 685° C. before inspection.

Figure 6:
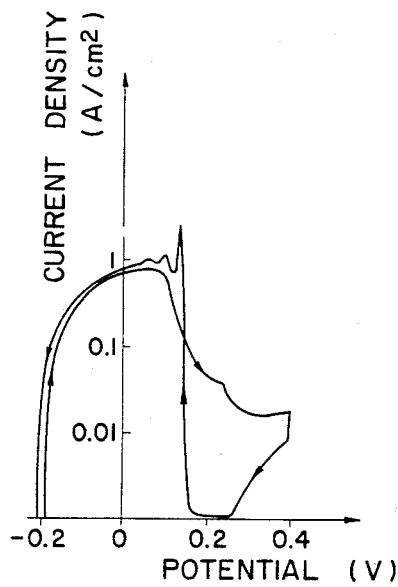
FIG. 6 is a similar graph of a polarization curve obtained in Example 3.

The anode polarization curve obtained is shown in FIG. 6.

EXAMPLE 4

Figure 8:
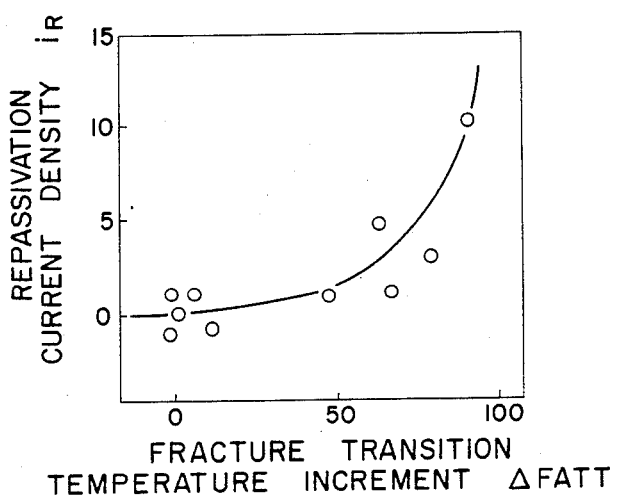
FIG. 8 is a graph indicating a relationship between a repassivation current and fracture transition temperature increment.

Test pieces were collected from several regions used at varying temperatures in high and intermediate pressure stage portions of the same steam turbine rotor as was used in Example 1, and the repassivation current and fracture transition temperature thereof were respectively measured. As a result, the relationship shown in FIG. 8 was obtained. In FIG. 8, the ordinate indicates the repassivation current density $i_R$, which is expressed in terms of the quotient of the repassivation current divided by the area measured, while the abscissa indicates the fracture transition temperature increment $\Delta FATT$ which is expressed in terms of the increments of the fracture transition temperatures of the respective regions from that of the coupling portion wherein no embrittlement has occurred, the fracture transition temperature of the coupling portion being determined as zero. It is possible to evaluate quantitatively the degree of temper brittleness of a test piece by measuring the repassivation current thereof and comparing the data thus obtained with the relationship illustrated in FIG. 8.

EXAMINATION OF EXAMPLES 1, 2, AND 3

As can be seen from FIG. 4 with respect to the sample (intermediate pressure stage portion) wherein embrittlement occurred, FIG. 5 with respect to the sample (coupling portion) wherein no embrittlement occurred, and FIG. 6 with respect to the sample (de-embrittled material) wherein embrittlement was eliminated, when embrittlement has occurred, the minimum portion "d" of the curve is relatively high, and the repassivation current $I_f$ flows. On the contrary, when no embrittlement occurs, the minimum portion "e" of the curve becomes low, and the repassivation current is zero. Thus, it is apparent that it is possible to detect the presence or absence of temper brittleness by detecting the repassivation current.

We have carried out the following three tests in order to further confirm the effects descried above.

In a first test, for the same test pieces as those of Examples 1, 2, and 3 described above, polarization curves 1, 2, and 3 were respectively prepared. In this case, the operation was discontinued at the points of the minimum portion "d" or "e" of the curves, and microscopic observation of the sample surface was carried out.

As a result, at the surface of the sample (intermediate pressure stage portion) wherein embrittlement occurred, no passive film was formed along the grain boundary, and the sample was etched in the form of grooves. On the other hand, at the surface of samples having no temper brittleness (coupling portion and de-embrittled material), a passive film was formed on the entire surface. This confirms that a repassivation current flows because of the textural change, i.e., temper brittleness.

Figure 7A:
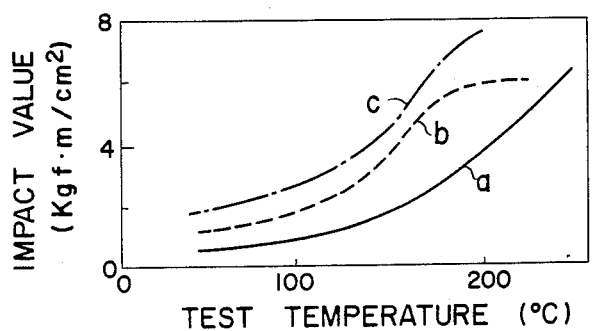
FIG. 7(a) is a graph indicating a temperature-impact value curve.

In a second test, for the same test pieces as those of Examples 1-3 described above, the relationship between temperature and Charpy impact value was tested. The results are shown in Table 7(a). Curves a, b and c in FIG. 7(a) show test temperature-impact value curves of the intermediate pressure stage portion, coupling portion and de-embrittled material, respectively. As can be seen from this figure, in the case of the intermediate pressure stage portion, temper brittleness occurs apparently, whereas in the case of the other two samples this temper brittleness does not occur.

Figure 7B:
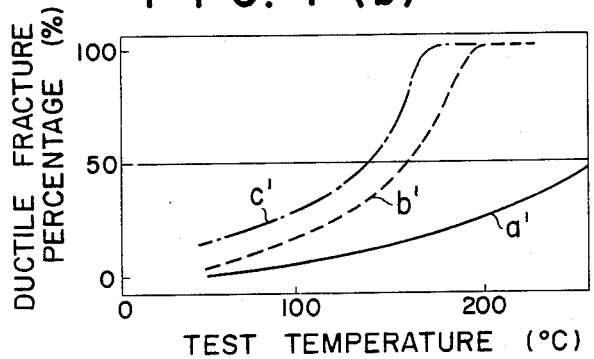
FIG. 7(b) is a graph indicating a temperature-ductile fracture percentage curve.

In a third test, for the same test pieces as those of Examples 1, 2, and 3 described above, the ratio of the ductile fractured surface area to the total fracture area, i.e., ductile fracture percentage, was measured from the fractured surface after Charpy impact test; and the relationship between temperature and ductile fracture percentage was determined. The results are shown in FIG. 7(b). Curves a', b' and c' in FIG. 7(b) show test temperature-ductile fracture percentage curves of the intermediate pressure stage portion, coupling portion and de-embrittled material, respectively.

As can be seen from this figure, the fracture transition temperature corresponding to a ductile fracture percentage of 50% moves to the higher side in the case of the intermediate pressure stage portion, whereas it is on the lower side in the case of the coupling portion and the de-embrittled material. Accordingly, it is further confirmed that there was no embrittlement in the coupling portion and the de-embrittled material, whereas there was embrittlement in the other sample.

According to the present invention, the following advantages are afforded:

(a) It is possible to provide a novel electrochemical detection method which is different in principle from the prior art methods for detecting temper brittleness occurring with passage of time.

(b) It is possible to detect temper brittleness with time non-destructively without carrying out any destructive test of the prior art detection methods.

(c) The use of a portable apparatus as an apparatus for the measurement of a polarization curve facilitates the detection of temper brittleness with time of immovable large-size steel products.

(d) The detection method of the present invention is a non-destructive test. If a portable detection apparatus is used, it is possible to carry out inspection with regard to temper brittleness with time during periodical inspection for the purpose of maintenance.

What is claimed is:

1. A method of detecting embrittlement of a heat-resisting steel which comprises evaluating the brittleness of the heat-resisting steel on the basis of the repassivation current value obtained by the steps of:
    (a) connecting the heat-resisting steel as the anode of an anode polarization curve measuring apparatus wherein an aqueous solution containing an organic acid and an alkylbenzene sulfonic acid or its salt is used as an electrolytic solution; and
    (b) raising the anode potential from an active region to a passive region and thereafter lowering the anode potential to measure the repassivation current value.

2. The method according to claim 1 wherein the organic acid is picric acid.

3. The method according to claim 1 wherein the alkylbenzene sulfonate is sodium trimethylbenzene sulfonate.

4. The method according to claim 1 wherein the alkylbenzene sulfonic acid or its salt is used in an amount of from 0.01 to 10 moles per mole of the organic acid.

* * * * *